United States Patent
Tennant et al.

(10) Patent No.: US 7,624,873 B2
(45) Date of Patent: Dec. 1, 2009

(54) DIAGNOSTIC SPECIMEN SHIPPING KIT

(75) Inventors: Pamela J. Tennant, Morrow, OH (US);
Kurt H. Tennant, Morrow, OH (US)

(73) Assignee: Tennant Packaging Corporation,
Lebanon, OH (US)

( * ) Notice: Subject to any disclaimer, the term of this patent is extended or adjusted under 35 U.S.C. 154(b) by 359 days.

(21) Appl. No.: 11/471,432

(22) Filed: Jun. 20, 2006

(65) Prior Publication Data

US 2007/0289894 A1  Dec. 20, 2007

(51) Int. Cl.
*B65D 69/00* (2006.01)
*B65D 81/02* (2006.01)
*B65D 81/20* (2006.01)
*F25D 23/00* (2006.01)

(52) U.S. Cl. .................... 206/569; 206/523; 206/524.8; 220/592.1

(58) Field of Classification Search ................. 206/569, 206/305, 524.8, 523, 591–594, 446, 443, 206/593, 524, 521; 220/495.01, 495.06, 220/592.01, 592.02, 592.1; 383/38
See application file for complete search history.

(56) References Cited

U.S. PATENT DOCUMENTS

| | | | | |
|---|---|---|---|---|
| 3,117,513 A | | 1/1964 | Burnett et al. ............... 110/215 |
| 3,968,620 A | | 7/1976 | Keltner ......................... 53/434 |
| 4,240,547 A | | 12/1980 | Taylor ........................ 206/204 |
| 4,418,514 A | | 12/1983 | Spann ......................... 53/436 |
| 4,932,533 A | * | 6/1990 | Collier ........................ 206/569 |
| 4,947,658 A | | 8/1990 | Wheeler et al. ............... 62/372 |
| 5,236,088 A | | 8/1993 | Dhority et al. ............... 206/438 |
| 5,366,080 A | * | 11/1994 | Carstersen et al. .......... 206/723 |
| 5,405,012 A | * | 4/1995 | Shindler et al. ............. 206/569 |
| 5,441,170 A | | 8/1995 | Bane, III ................ 229/103.11 |
| 5,450,948 A | * | 9/1995 | Beausoleil et al. .......... 206/204 |
| 5,553,708 A | * | 9/1996 | Lawrence et al. ........... 206/419 |
| 5,615,795 A | * | 4/1997 | Tipps ..................... 229/185.1 |
| 5,620,098 A | | 4/1997 | Boos et al. .................. 206/525 |
| 5,791,476 A | * | 8/1998 | Stekloff ...................... 206/521 |
| 5,924,302 A | | 7/1999 | Derifield .................... 62/457.2 |
| 5,931,303 A | | 8/1999 | Salvadori .................... 206/570 |
| 5,979,693 A | | 11/1999 | Bane, III ................. 220/592.2 |
| 6,085,907 A | * | 7/2000 | Hochmeister et al. ....... 206/569 |
| 6,092,654 A | * | 7/2000 | Webb ......................... 206/320 |
| 6,128,889 A | | 10/2000 | Fuss ........................... 53/472 |
| 6,325,281 B1 | | 12/2001 | Grogan .................. 229/103.11 |
| 6,519,968 B1 | | 2/2003 | Konarski ...................... 62/371 |
| 6,868,982 B2 | | 3/2005 | Gordon ................. 220/592.23 |
| 7,306,102 B2 | * | 12/2007 | Chang ........................ 206/523 |
| 2001/0045372 A1 | | 11/2001 | Curley et al. ................ 206/525 |
| 2002/0162767 A1 | * | 11/2002 | Ohtsubo ................... 206/524.8 |
| 2003/0012701 A1 | | 1/2003 | Sangha et al. ............... 422/102 |
| 2003/0183550 A1 | * | 10/2003 | DiLiberto, Jr. ........... 206/524.8 |

* cited by examiner

*Primary Examiner*—Mickey Yu
*Assistant Examiner*—Melissa L Lalli
(74) *Attorney, Agent, or Firm*—Alfred J. Mangels

(57) ABSTRACT

A shipping container for shipping diagnostic specimens. An outer container includes inner foam panels that define an inner cavity enclosed by a closed cell polymeric foam for receiving items to be shipped. The inner cavity has an H-shaped transverse cross section for receiving specimen vials that can be packaged in a polymeric bag having several side-by-side compartments for receiving specimen vials. A freezable material is placed within the inner cavity and adjacent to the specimens to maintain the specimens packed within the container below a predetermined temperature during shipment. The foam defining the inner cavity provides insulation to aid in maintaining the temperature of the contents.

10 Claims, 5 Drawing Sheets

DIAGNOSTIC SPECIMEN SHIPPING KIT

BACKGROUND OF THE INVENTION

1. Field of the Invention

The present invention relates to a shipping kit for shipping diagnostic specimens in compliance with regulatory requirements. More particularly, the present invention relates to a diagnostic specimen shipping kit that is initially in collapsed, flattened form for convenient arrangement of a number of such kits as a shipping unit for shipment in a shipping container to a user. The kit contains components for assembling an insulated specimen shipment container and includes a source of coolant for placement within the container for maintaining specimens below a required temperature during shipment and prior to analysis of the specimens by an analytical laboratory.

2. Description of the Related Art

The shipment of diagnostic specimens must conform with specific shipping regulations imposed by the carrier of the shipment, for protection of those who handle the shipment during transit and also the general public. For example, the U.S. Postal Service has issued mailing standards in its Domestic Mail Manual, section 601.10.17 that identifies infectious or hazardous substances and prescribes packaging requirements for such materials. Thus, blood specimens and other bodily fluids for clinical laboratory testing are generally categorized as diagnostic specimens for the shipment of which the postal packaging regulations must be followed. The specimens must be packaged in accordance with 49 C.F.R. § 173.196.

Previous packaging for such materials was in the form of pre-formed package components. The individual, pre-formed components often were separately packaged. Additionally, the components as shipped to a user occupied considerable space and were therefore inconvenient and more costly to ship to a user of the packaging materials. Moreover, they often utilized rigid foam components to provide the desired protection against shock and impact damage and also to provide insulation value for control of the product temperature during shipment, which increased the size of the component packages as shipped to the user.

There is thus a need for an improved and more convenient shipping materials kit for use in connection with diagnostic specimen shipments. There is also a need to reduce the size of the package components that are provided to users and thereby to allow more economical shipment of the packaging components to the user, and also to provide the components of a single shipping unit in a ready-to-use single package. The present invention provides such an improved shipping kit.

SUMMARY OF THE INVENTION

Briefly stated, in accordance with one aspect of the present invention, a diagnostic specimen shipping kit is provided. The kit includes an outer container defining a first cavity and having a pair of opposed, spaced parallel side walls, opposed spaced parallel front and back walls arranged perpendicular to the side walls a bottom wall, and a top panel hingedly connected with the rear wall to define a top cover. An inner container defining a second cavity is positioned within the first cavity, wherein the inner container is formed from a flexible polymeric foam having a predetermined thickness, the second cavity having an H-shaped opening in a transverse plane passing through the outer container and substantially parallel to the outer container bottom wall to define a pair of spaced inner compartments for receiving items to be shipped. The inner compartments are interconnected by an intermediate open region having a smaller volume than that of either of the inner compartments, and are closed by upper and lower spaced, parallel foam panels that define upper and lower boundaries of the H-shaped cross section, respectively.

In accordance with another aspect of the present invention, a shipping kit including foamed panels is provided that is initially in substantially flattened form for shipment to a user.

BRIEF DESCRIPTION OF THE DRAWINGS

The structure, operation, and advantages of the present invention will become further apparent upon consideration of the following description, taken in conjunction with the accompanying drawings in which.

DESCRIPTION OF THE PREFERRED EMBODIMENTS

Figure 1:
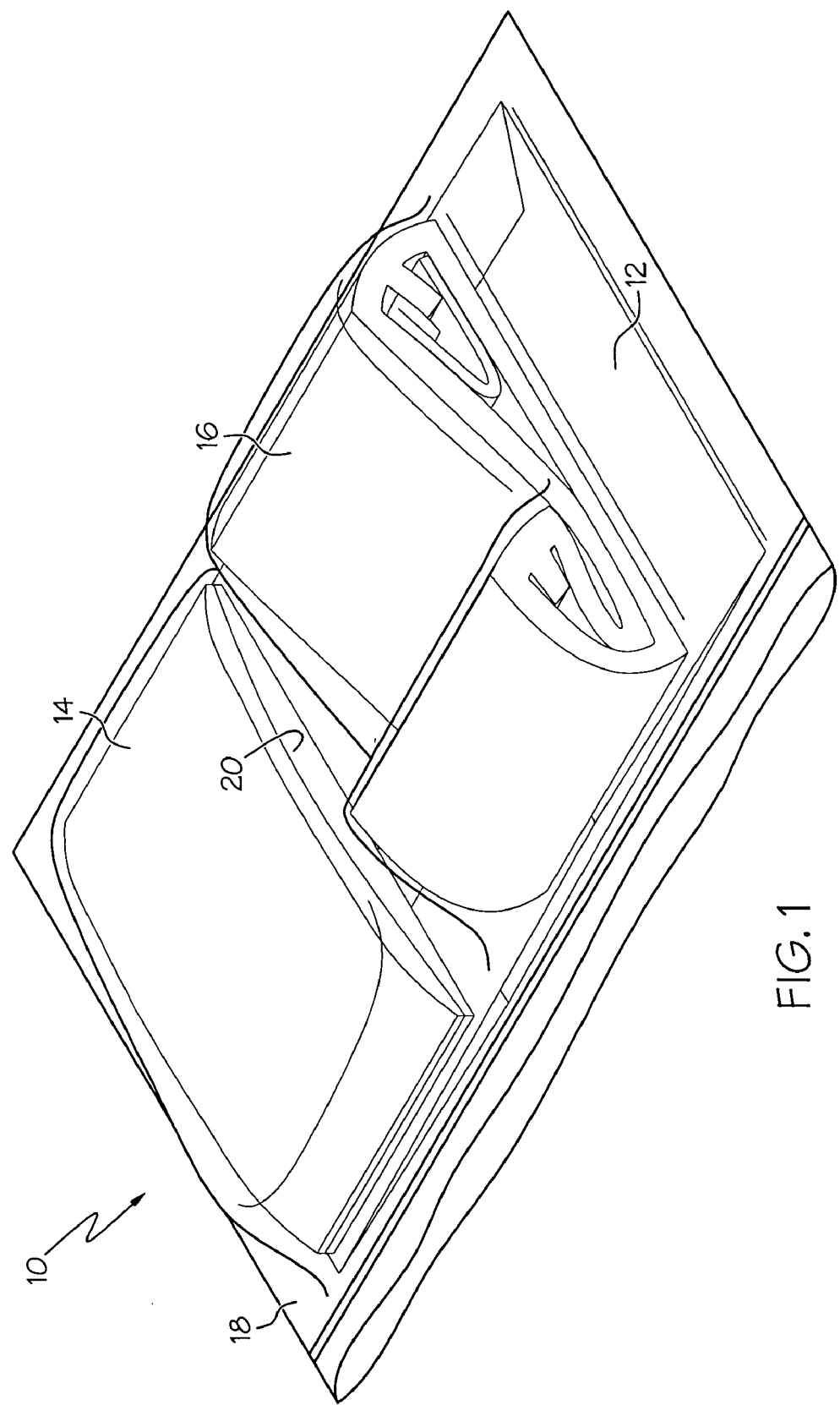
FIG. 1 is a perspective view of a shipping container kit in accordance with one embodiment of the invention, arranged for shipment to a user.

Referring now to the drawings, and particularly to FIG. 1 thereof, there is shown in substantially flattened form a shipping container kit 10 that contains the components for shipping diagnostic specimens in a manner that meets the shipping material and structural requirements for such specimens. The kit includes a knocked-down container blank 12 and resilient insulation components 14, 16 for physically protecting shipped goods and also for protecting them from ambient temperature extremes. Although the kit is especially adapted for shipping diagnostic specimens, it is not limited to diagnostic use.

Kit 10 includes an outer, transparent plastic bag 18 that serves as an outer wrapper or packet for enclosing the components of the shipping kit. Bag 18 is made from a suitable plastic film material that is capable of being heat sealed closed, and that also has sufficient gas barrier properties to maintain a vacuum for a period of at least about 8 to 12 weeks after it has been substantially evacuated. Examples of suitable plastic films include laminated or coextruded films. The film can have a thickness of from about 0.001 in. to about 0.003 in. in order to protect the contents from dirt and other contaminants during shipment of the kit to a user prior to use, and also to minimize possible bag punctures during shipment or during handling before use, which would destroy the vacuum within a sealed bag.

As shown in FIG. 1, the contents of kit 10 include a flat, preformed, knockdown container blank 12. The blank is in such a form that it can be readily erected from a flat condition to form a rectangular container in the form of a box without the need for adhesively joining of panels. Container blank 12 can advantageously be formed from double-sided container board having an intermediate corrugated liner sandwiched between inner and outer layers, as will be appreciated by those skilled in the art. Corrugated board having a burst strength of at least about 200 lb. can be utilized to provide adequate protection to the packaged contents during shipment. The structure and contents of the erected container will be further described hereinafter.

In the course of assembly of the components of kit 10 for shipment to a shipping kit user, the remaining components of a complete shipping kit are placed on the of surface container blank 12. Included are an inner, flexible foam sidewall liner or sleeve 16, an inner, flexible foam bottom liner pad 14 and an inner, flexible foam top liner pad 20. The foamed material components are intended to surround and enclose the shipped goods to protect them from impact damage, and also to serve as insulation to protect the shipped goods from ambient temperature extremes during shipment. Also included, but not visible in FIG. 1 because it is placed between bottom liner pad 20 and container blank 12, is a packet of freezable material. The packet can be placed in a freezer and frozen by the kit user for inclusion within an assembled shipping package, adjacent to or in contact with the specimens to be shipped, in order to maintain the shipped items at a desired temperature during shipment. Also included, but not visible in FIG. 1, is an inner plastic bag that can serve as an inner liner between the inner side, front, back, and bottom wall surfaces of the interior of the erected shipping container and the foam pads 14, 20 and foam sleeve or liner 16. Additional kit materials that can also be placed between the foam pads and the container blank and that can be utilized as components of a completed specimen shipping kit can include such items as specimen bags for holding diagnostic specimen vials, a top tray for placement of orders or instructional or identifying materials to accompany the specimens and for microscope slides, protective sealable envelopes for microscope slides, hematology packs, adhesive-carrying sealing strips for sealing the inner bag and the assembled container, shipping and biohazard labels for placement on the outside of the container when ready for shipment, and the like.

In preparing the kit for shipment to a kit user, the several components are positioned relative to each other as shown in FIG. 1 and the components are then placed in outer bag 18. The air within outer bag 18 is then evacuated, which because of the pressure differential between the pressure in the interior of the bag and the ambient pressure, causes the bag sides to be drawn toward each other over the kit components. The pressure differential is also sufficient to cause the foam components within the bag to be compressed to a significantly thinner state than their original, uncompressed state, thereby reducing the overall thickness of the packaged kit 10. After the outer bag contents have been compressed and the bag sidewalls have been drawn against the kit contents, the open end of outer bag 18 is heat sealed closed. A number of the resulting flattened shipping kits can be packed in side-by-side relationship within in a further rectangular container for shipment to the kit user.

Figure 2:
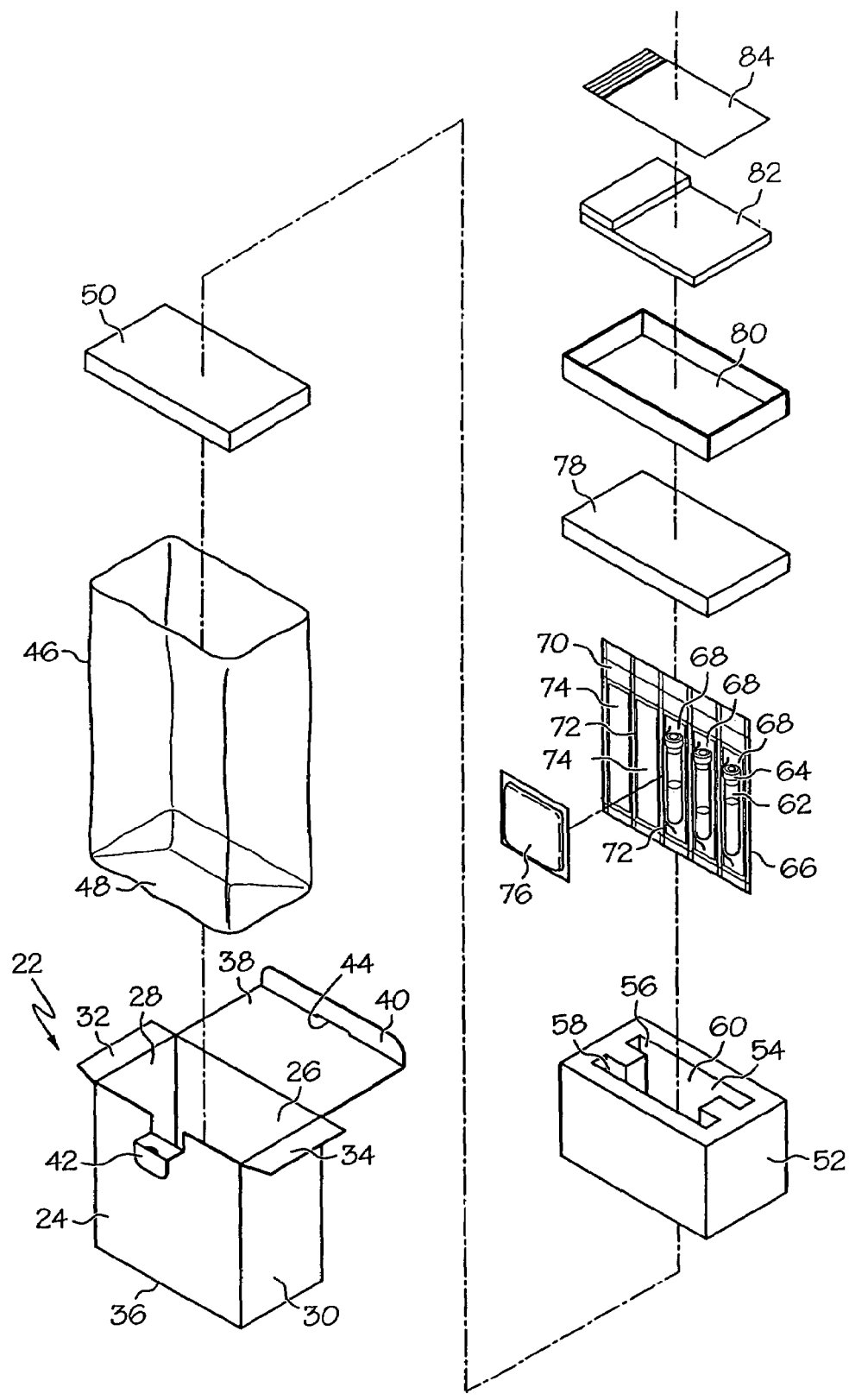
FIG. 2 is an exploded perspective view of the kit shown in FIG. 1 with the components in assembled form and shown in their relative positions when ready for assembly into a completed shipping container.

The various components of shipping kit 10 are shown in exploded form and in their uncompressed condition in FIG. 2. When container blank 12 is erected it forms a box-like container 22 that defines a rectangular enclosure that includes opposed, parallel front and back walls 24, 26, respectively, opposed, parallel side walls 28, 30, respectively, that include respective side flaps 32, 34, a bottom wall 36 formed by suitably interconnected panels that together define a closed container bottom, and a top cover panel 38 including a front tuck flap 40. Front wall 24 includes an integral locking flap 42 that is subsequently received in a slot 44 formed in top cover panel 38 to lock the top cover panel in its closed position when shipping container 22 is packed and closed for shipment.

Placed within erected shipping container 22 and serving as an inner liner therefor is a flexible, polymeric inner bag 46. Bag 46 is a gusseted structure to fit within the rectangularly-shaped shipping container 22 and is so sized as to provide a liner that is in surface-to-surface contact with the inner surfaces of each of front and back walls 24, 26, with each of side walls 30, 32, and with bottom wall 36. As shown in FIG. 2, inner bag 46 has a height dimension that is greater than the height dimension of the container front, back, and side walls, so that the excess bag material can be folded over to close the bag when the desired contents have been placed within the bag while it is within shipping container 22. Inner bag 46 can be formed from a film of polymeric material, such as polyethylene, polypropylene, and the like.

Positioned inside inner bag 46 and covering the bag bottom 48 is a rectangular foam bottom panel 50 that completely overlies the inner surface of container bottom wall 36 and fits snugly against the front, back, and side walls of shipping container 22. In that regard, bottom panel 50 has substantially the same dimensions as the inner dimensions of container bottom wall 36, and it extends between each of container front and back walls 24, 26, and container side walls 30, 32.

The next component that is placed inside inner bag 46 and is arranged to rest against foam bottom panel 50 is foam sidewall sleeve 52. Sidewall sleeve 52 is a tubular component and has a height that is less than that of the front, back, and side walls of shipping container 22. It is of generally rectangular form to fit within shipping container 22 and to lie against the inner surfaces of front and back walls 24, 26, and also against the inner surfaces of side walls 30, 32. A substantially H-shaped opening 54 is provided in and extends longitudinally through sidewall sleeve 52. Opening 54 defines a first sample receiving region 56 and a second sample receiving region 58 that is spaced from the first receiving region. The respective sample receiving regions serve for receiving diagnostic materials in the form of specimens that are to be shipped to an analytical laboratory, or the like. Each of first and second sample receiving regions has substantially the same dimensions and substantially the same volume.

Between first and second sample receiving regions 56, 58 is an intermediate region 60 having the same height as that of each of the first and second sample receiving regions 56, 58, but having a larger thickness in the front-to-back direction of shipping container 22 and a smaller width in the side-to-side direction of the shipping container. First and second sample receiving regions 56, 58 are intended for receiving suitably packaged diagnostic specimens. Intermediate region 60 is intended for the placement of a freezable pouch for maintaining diagnostic specimens below a predetermined temperature during shipment. Alternatively, intermediate region 60 can be left empty if the packaged specimens need not be maintained in a cool condition, or it can serve to receive additional specimens, if desired.

The diagnostic specimens, which when in liquid form are packaged in tubular glass vials 62 that include closure caps 64, are placed in a vial holder in the form of a specimen bag 66 having several side-by-side, sleeve-like channels or compartments 68 for receiving the tubular vials. Specimen bag 66 is formed from two sheets of a tough polymeric material having liquid and gas barrier properties, to protect the vial contents. Bag 66 can be sealed closed by an adhesive strip 70 containing a pressure sensitive adhesive layer and having an overlying, peelable, protective release layer. Compartments 68 are defined by several spaced, parallel, linear heat seals 72 and contain absorbent strips 74 as liners for receiving and holding any fluid that might leak from an incompletely closed specimen vial. Specimen bag 66 can advantageously be formed from two sheets of an oriented polyamide film having a polyethylene layer. The polyethylene layered sides face each other and allow the outer edges of the sides of the bag to be heat sealed together; they also to allow the inner channels or compartments to be formed by the spaced, parallel, heat seals.

One or more freezable pouches 76 can be provided for maintaining the specimens contained in specimen bag 66 below a predetermined temperature during shipment. Such freezable pouches are readily commercially available and can contain a freezable liquid or a freezable gel in a sealed, impervious film pouch. They can also be dry ice packets. Alternatively, such pouches can contain hydratable crystals that are contained in a porous envelope to allow hydration of the contents for subsequent freezing. Such crystal-containing pouches are distributed under the name "Proxy Ice," and are available from Proxy Packaging, Houston, Tex. The freezable pouch can be so sized that it fits snugly within intermediate region 60 of foam sidewall sleeve 52 by having a pouch width that is slightly larger than the width of intermediate region 60 when considered in a side-to-side direction of shipping container 22, for an interference-type fit.

Placed above specimen bag 66 is a top foam pad 78 that overlies and completely covers the upper, H-shaped opening 54 in foam sidewall sleeve 52. Top foam pad 78 can be the same size and shape as that of bottom foam pad 50, and together those pads and foam sidewall sleeve 52 completely enclose specimen bag 66 in a cushioned and an insulated manner.

Top and bottom foam pads 78, 50 and foam sidewall sleeve 52 can be formed from a flexible, compressible, resilient, closed cell polymeric foam having a density of at least about 1.0 lb/ft$^3$ to provide sufficient cushioning and sufficient insulation qualities to adequately protect the diagnostic specimens and maintain them below a predetermined temperature, such as from about 32° F. to about 65° F. The foam pads and the foam sleeve can be die cut, contour cut, or compression cut from the foam material.

Bottom and top foam pads 50, 78 have a thickness, and the outer walls of foam sidewall sleeve 52 have a wall thickness of at least about 1.0 in. and can be as thick as about 2.0 in., if desired. A closed or open cell resilient foam available from various polyurethane foam manufacturers has been found to be suitable for maintaining specimens below about 65° F. for about 24 hours. Other commercially available foamed polymers having similar properties would also be suitable.

A flat tray 80 formed from a scored sheet of corrugated board, or the like, to form tray side walls and tray end walls overlies top foam pad 78. Tray 80 serves as a receptacle for receiving a foam slide carrier pad 82 or a slide bag 84 for microscope slides containing diagnostic specimens. And although the space enclosed by top and bottom foam pads 78, 50 and by foam sidewall sleeve 52 defines a refrigerated enclosure, the volume defined by tray 80 is at ambient temperature.

Figure 3:
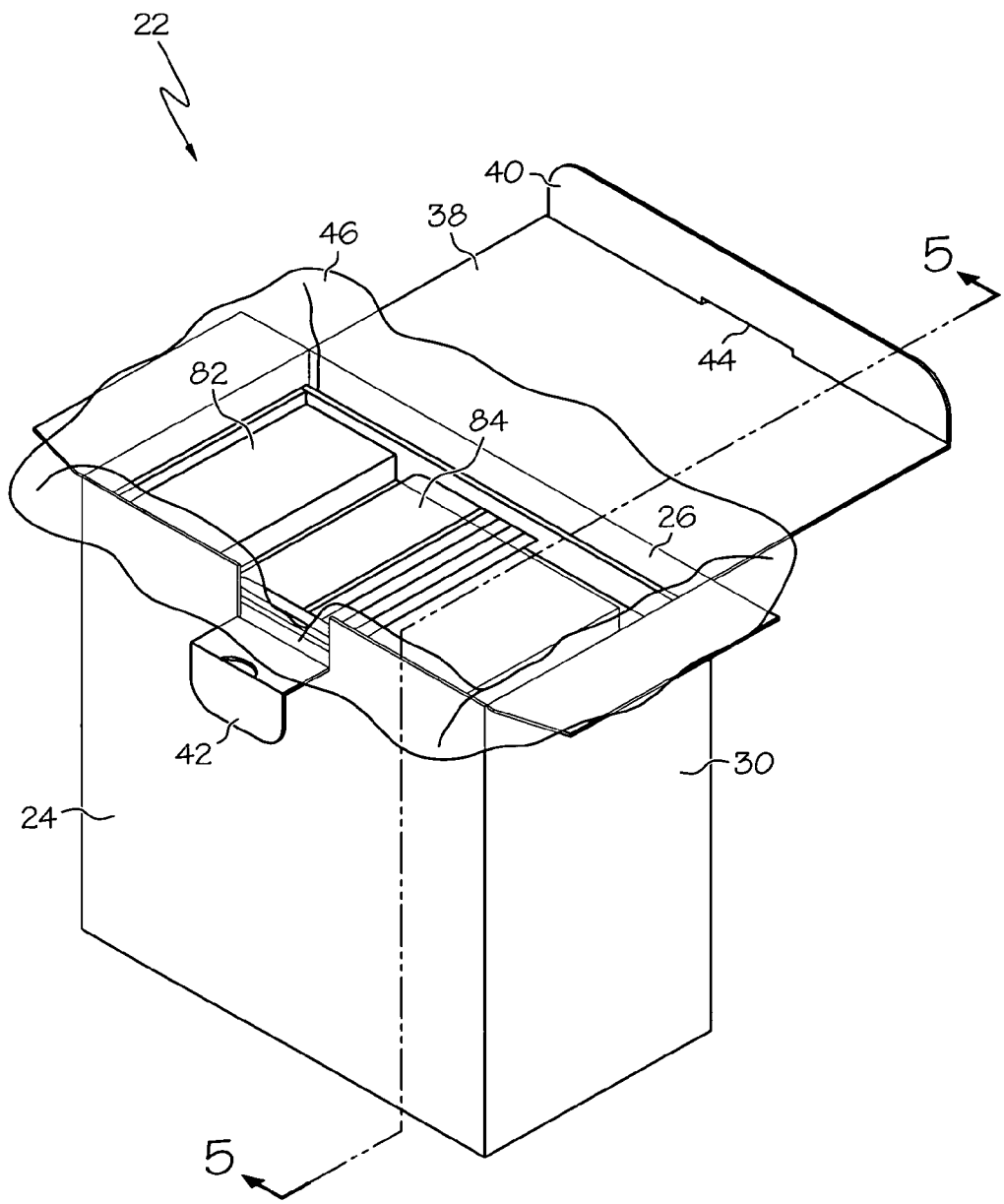
FIG. 3 is a top perspective view of the assembled shipping container with the several components in place for shipment and prior to closing and sealing of an inner liner bag and closing of a top panel.
Figure 4:
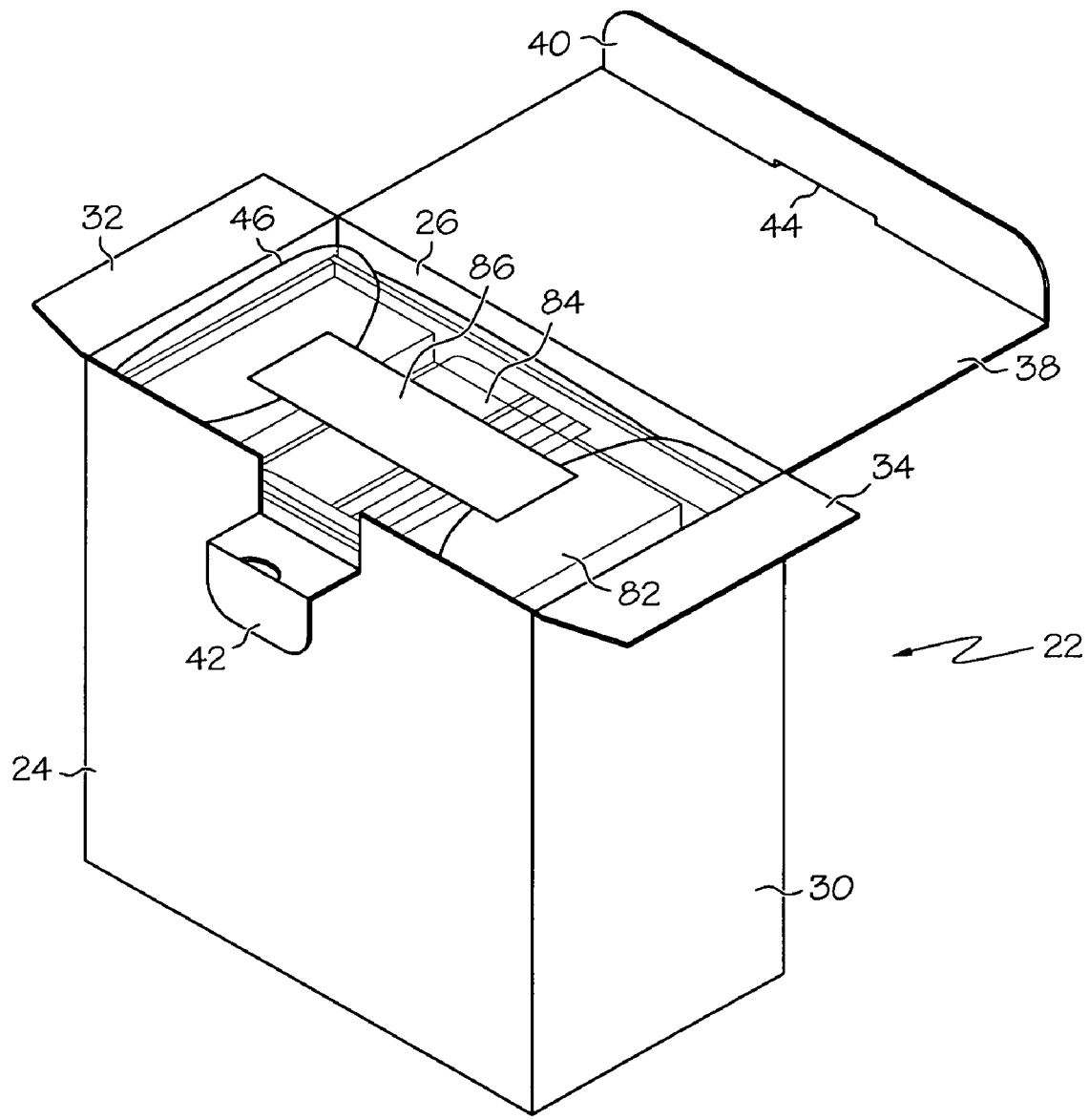
FIG. 4 is a top perspective view of the assembled shipping container of FIG. 3 after sealing of the inner liner bag and before closure of the container opening by the top panel.

Once in its assembled form with the several components placed within shipping container 22 in the sequence illustrated in the exploded view shown in FIG. 2, the completed package is as shown in FIG. 3 and is ready for closing. Closing is effected by inwardly folding over upon itself the exposed, upper end portion of inner bag 46, as shown in FIG. 4, and applying a tape seal over the folded portion to close the upper end of the inner bag. Thereafter container end flaps 32, 34 are folded inwardly to overlie inner bag 46, and then top cover panel 38 is folded over to overlie the end flaps. The tuck flap 40 is inserted into the container adjacent the inner surface of container front wall 24 to close the top of the shipping container. Front locking tab 42 is then inserted into slot 44 in top cover panel 38 to hold the top cover panel in the closed position. A suitable sealing tap or strip (not shown) can then be applied over the top cover panel to securely maintain the shipping container in a closed condition until it is to be opened at an analytical laboratory.

Figure 5:
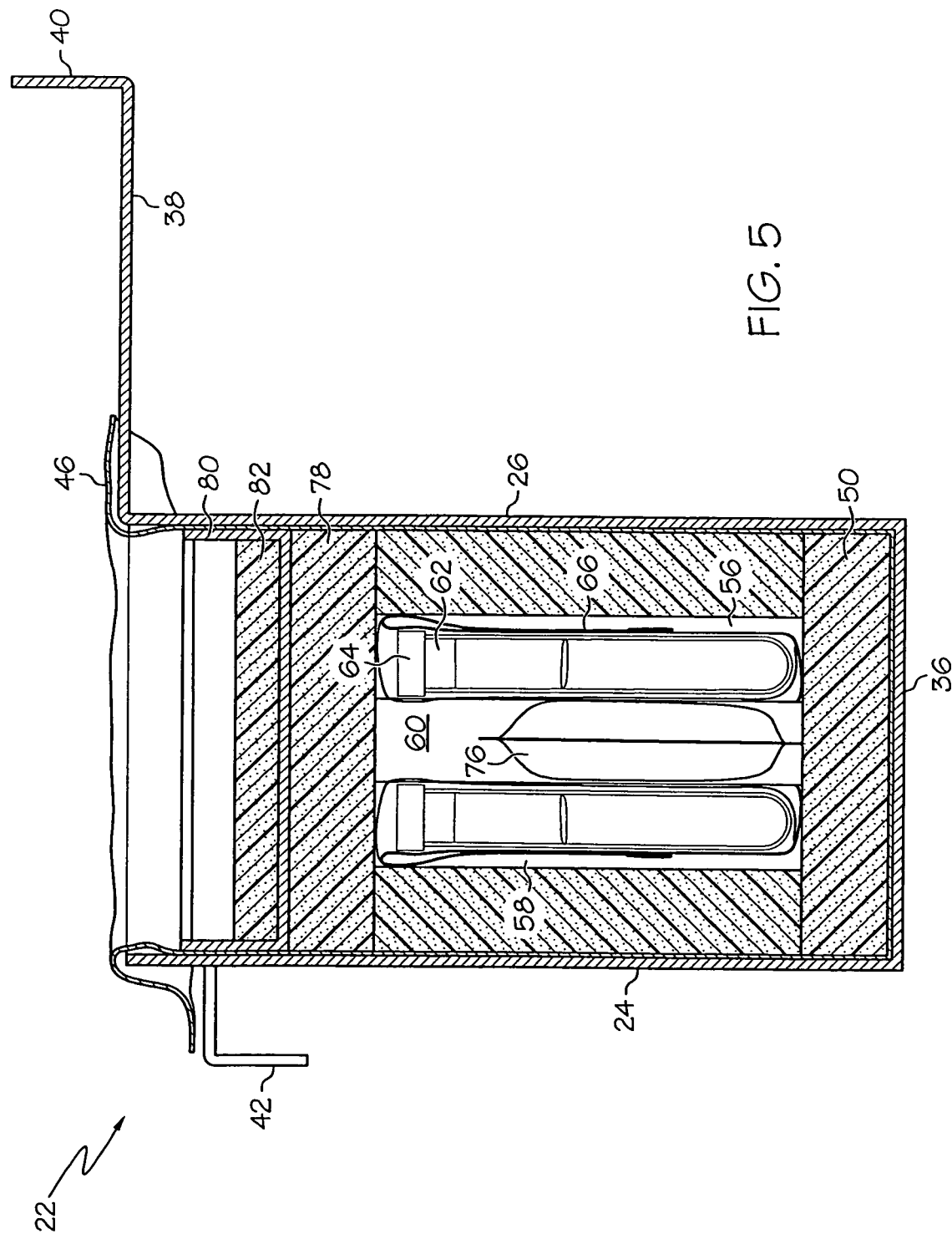
FIG. 5 is a cross-sectional view of an assembled, but not yet closed, shipping container taken along the line 5-5 of FIG. 3.

FIG. 5 is a vertical cross-sectional view through the shipping container from front to back, when it is in its substantially packed condition but still open, showing a specimen bag 66 and an adjacent freezable pouch 76 within shipping container 22. As can be seen, both the specimen pouch and the freezable pouch are surrounded by the respective foam panels, which serve to cushion them against impact loads, to insulate them, and to maintain them at or below a desired temperature during shipping. Although only one specimen pouch is shown, it is apparent that two or more such pouches can be carried within the shipping container.

As will be readily apparent, the disclosed arrangement provides a compact and effective shipping arrangement for shipping items, such a diagnostic specimens, that must be maintained at a controlled temperature. And although the foregoing description contemplates use of the invention for the shipment of diagnostic and diagnostic specimens, it can also be used for the shipment of other materials or goods.

Although particular embodiments of the present invention have been illustrated and described, it will be apparent to those skilled in the art that changes and modifications can be made without departing from the spirit of the present invention. Accordingly, it is intended to encompass within the appended claims all such changes and modifications that fall with the scope of the present invention.

What is claimed is:

1. A shipping kit for diagnostic specimens, said shipping kit comprising:
   a) a flat, die cut blank of double faced corrugated board for assembly into a box;
   b) a flat, die cut paperboard blank to define a combined spacer and tray;
   c) an inner flexible plastic bag to define a liner for placement within the box;
   d) flexible, resilient open cell foam top and bottom pads in rectangular form;
   e) a unitary inner, flexible, resilient open cell foam side panel unit of tubular, rectangular form and having an H-shaped inner opening in cross section;
   f) a compartmented flexible bag for receiving in separate side-by-side pockets several diagnostic specimens in individual tubular containers and in fluid form;
   g) a pouch containing a freezable material for placement within the side panel unit for maintaining the diagnostic specimens in a cooled condition during shipment;
   h) a slide mailer bag for specimen slides for placement in the tray;
   i) a slide mailer bag seal; and
   j) an outer, flexible plastic bag for containing and shipping the shipping kit components in flattened form and under vacuum to minimize shipping volume of the shipping kit components.

2. A shipping kit in accordance with claim 1, wherein the components are stacked one against another on the box blank.

3. A shipping kit in accordance with claim 2 wherein the stacked components are placed in stacked form within the flexible plastic outer bag.

4. A shipping kit in accordance with claim 3 wherein air within the flexible plastic outer bag has been substantially evacuated to draw bag sidewalls against and to substantially compress the foam top and bottom pads and the side panel unit to reduce thickness.

5. A shipping kit in accordance with claim 4, wherein the flexible plastic outer bag has been sealed closed to maintain the substantially evacuated condition of the outer bag.

6. A shipping kit for diagnostic specimens, said shipping kit comprising:
   a) a flat, die cut blank of double faced corrugated board for assembly into a box;
   b) a flat, die cut paperboard blank to define a combined spacer and tray;
   c) an inner flexible plastic bag to define a liner for placement within the box;
   d) flexible, resilient open cell foam top and bottom pads in rectangular form;
   e) a unitary inner, flexible, resilient open cell foam liner unit of tubular form and open at both ends;
   f) a compartmented, flexible specimen bag for receiving in separate side-by-side pockets several diagnostic specimens in individual tubular containers and in fluid form;
   g) a pouch containing a freezable material for placement within the side panel unit for maintaining the diagnostic specimens in a cooled condition during shipment;
   h) a slide mailer bag for specimen slides for placement in the tray;
   i) a slide mailer bag seal; and
   j) an outer, flexible plastic bag for containing and shipping the shipping kit components in flattened form and under vacuum to minimize shipping volume of the shipping kit and its components.

7. A shipping kit in accordance with claim 6, wherein the components overlie a flattened surface of the box blank.

8. A shipping kit in accordance with claim 7, wherein the components are in flattened relationship overlying the flattened surface of the box blank within the flexible plastic outer bag.

9. A shipping kit in accordance with claim 8, wherein air within the flexible plastic outer bag has been substantially evacuated to draw opposed sidewalls of the outer bag against and to substantially compress the foam top and bottom pads and the liner unit to reduce thickness.

10. A shipping kit in accordance with claim 9, wherein the flexible plastic outer bag has been sealed closed to maintain the substantially evacuated condition of the outer bag and to maintain the contents of the outer bag in compressed form.

* * * * *